United States Patent [19]

Babiak et al.

[11] Patent Number: 4,952,710
[45] Date of Patent: Aug. 28, 1990

[54] CYCLOPENTENEHEPTENOIC ACID DERIVATIVES AND METHOD OF PREPARATION THEREOF

[75] Inventors: Kevin A. Babiak, Evanston; Arthur L. Campbell, Glenview both of Ill.

[73] Assignee: G. D. Searle & Co., Chicago, Ill.

[21] Appl. No.: 255,179

[22] Filed: Oct. 7, 1988

[51] Int. Cl.$^5$ ............................................. C07D 309/12
[52] U.S. Cl. .................................. 549/416; 549/414; 549/415; 549/214
[58] Field of Search ............... 549/423, 415, 414, 214, 549/416

[56] References Cited

FOREIGN PATENT DOCUMENTS 67-4572 7/1967 South Africa .

*Primary Examiner*—Nicky Chan
*Attorney, Agent, or Firm*—Paul D. Matukaitis; Mary Jo Kanady; Roger A. Williams

[57] ABSTRACT

This invention relates to a novel cyclopenteneheptenoic acid derivative having the following formula

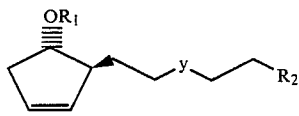

wherein $R_1$ is hydrogen, —COCH$_3$, —COCF$_3$, —CO—phenyl, or a hydroxyl protecting group such as tetrahydropyranyl, tetrahydrofuranyl, or tri-lower alkylsilyl;

wherein $R_2$ is —CH$_2$OR$_1$, —COOH, —COOR, —CHO, —CH$_2$—OSi(R$_{12}$)$_3$,

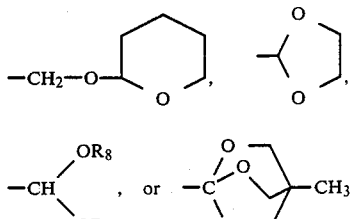

wherein R is lower alkyl and each $R_{12}$ is independently lower alkyl or aryl; and wherein Y is ethylene, cis-vinylene, trans-vinylene, or acetylene.

Also disclosed is a novel process for preparation of the above-defined cyclopenteneheptenoic acid derivative. This process involves coupling of a higher order cuprate complex with a chiral cyclopentene compound. The resultant product is particularly useful as a starting compound for high yield synthesis of optically active prostaglandins.

3 Claims, No Drawings

CYCLOPENTENEHEPTENOIC ACID DERIVATIVES AND METHOD OF PREPARATION THEREOF

BACKGROUND OF THE INVENTION

I. Field of Invention

This invention relates to novel organic compounds and a method of preparing same. In particular this invention relates to novel compounds of Formula I which are synthesized by coupling a higher order cuprate complex with a chiral cyclopentene. The resultant products from this coupling are particularly useful in the preparation of certain prostaglandins which exhibit optical activity.

II. Prior Art

The state of the art of higher order cuprate complexes is summarized in *Synthesis*. #4 p. 325, (1987) where higher order cuprate complexes of the formulae $R_tRCu(CN)Li_2$, $R_tCu(2\text{-thienyl})CNLi_2$, and $R_tRCu(SCN)Li_2$ and their use are disclosed. $R_t$ represents the group transferred to an organic compound to form a carbon to carbon bond in a subsequent reaction with the complex.

*JACS.* 94 7210 (1972) describes lithium copper vinyl complexes. *Prostazlandin Synthesis*, Academic Press, 1977, Chapt. 7 describes prostaglandin synthesis generally, including conjugate addition of organometallic derivatives to α-substituted cyclopentenones.

SUMMARY OF THE INVENTION

It is an object of this invention to provide novel organic compounds of Formula I which are useful as starting reagents in the preparation of optically active prostaglandins. More specifically it is an object of this invention to provide a chiral cyclopenteneheptenoic acid derivative which when utilized in the synthesis of certain prostaglandins results in a high purity of the optically active form of the desired prostaglandin.

It is another object of the invention to provide a novel process for the preparation of chiral cyclopenteneheptenoic acid derivatives and other chiral cyclopentene derivatives which are useful in the synthesis of optically active prostaglandins.

Accordingly, a broad embodiment of the invention is directed to a compound of the formula:

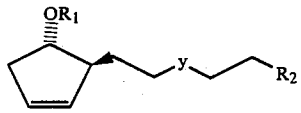
(I)

wherein $R_1$ is hydrogen, —COCH$_3$, —COCF$_3$, —COphenyl, or a hydroxyl protecting group such as tetrahydropyranyl, tetrahydrofuranyl, or tri-lower alkylsilyl;

wherein $R_2$ is —CH$_2$OR$_1$, —COOH, —COOR, —CHO, —CH$_2$OSi(R$_{12}$)$_3$,

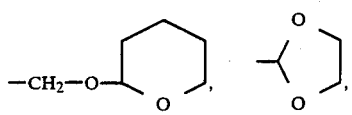

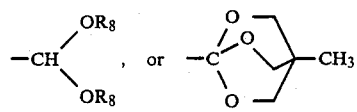

wherein R is lower alkyl;
wherein each $R_8$ is independently lower alkyl;
wherein each $R_{12}$ is independently lower alkyl or aryl;
wherein Y is ethylene, cis-vinylene, trans-vinylene, or acetylene.

Another embodiment of the invention is a process for the preparation of compounds of the formula:

(II)

comprising bringing into reactive contact a higher order cuprate complex of the Formula II:

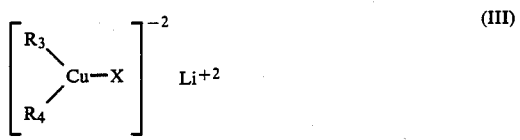
(III)

wherein:
(a) X is —CN, —SCN, —OSO$_2$CF$_3$, or —S—phenyl;
(b) R$_3$ is thienyl; and
(c) R$_4$ is —A—R$_9$ wherein A represents alkylene of from 1 to 8 carbon atoms, alkenylene of from 2 to 8 carbon atoms, or alkynylene of from 2 to 8 carbon atoms, and wherein R$_9$ is

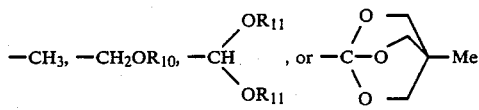

wherein R$_{10}$ is tetrahydropyranyl, ethylvinyl ether, or —Si(R$_{12}$)$_3$;
wherein R$_{11}$ is alkyl, alkylaryl, or —CH$_2$CH$_2$—; and
wherein each R$_{12}$ is independently lower alkyl or aryl with a chiral cyclopentene of the formula:

(IV)

wherein R$_5$ and R$_6$ are independently —OH or —OCOR$_7$ with each being bound to a chiral carbon; whereby either R$_5$ or R$_6$ is replaced by R$_4$ on the cuprate complex to form the compounds of Formula II; wherein R$_7$ is —CH$_3$, —C(CH$_3$)$_3$, —phenyl, or —CF$_3$.

These as well as other objects and embodiments will become evident from the following more detailed description of the present invention.

DETAILED DESCRIPTION OF THE INVENTION

The novel compounds encompassed by the instant invention provide useful starting reagents in the synthesis of optically active prostaglandins. These novel compounds can be described by the following general formula:

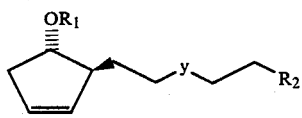
(I)

wherein R$_1$ is hydrogen, —COCH$_3$, —COCF$_3$, —CO—phenyl, or a hydroxyl protecting group such as tetrahydropyranyl, tetrahydrofuranyl, or tri-lower alkylsilyl;
wherein R$_2$ is —CH$_2$OR$_1$, —COOH, —COOR, —CHO, —CH$_2$—OSi(R$_{12}$)$_3$,

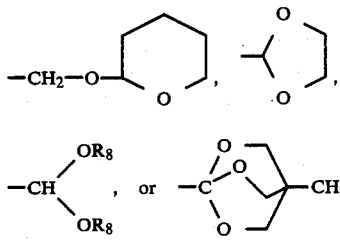

wherein R is lower alkyl and each R$_8$ is independently lower alkyl; and
wherein Y is —CH$_2$CH$_2$—("ethylene"),

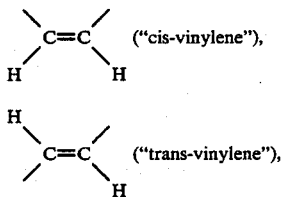

or —c≡c— ("acetylene").

By "lower alkyl" as used herein is meant straight and branched chain hydrocarbons having 1–8 carbon atoms.

By "alkenyl" as used herein is meant an unbranched acyclic hydrocarbon having at least one double bond and having 2–8 carbon atoms.

By "alkynyl" as used herein is meant an unbranched acyclic hydrocarbon having at least one triple bond and having 2–8 carbon atoms.

By "Thienyl" or "Th" is meant a compound having the formula:

By "aryl" is meant phenyl or benzyl.

Formula I illustrates that the compounds of the present invention may be derivatives of cyclopenteneheptanoic acid, cyclopenteneheptenoic acid, or cyclopenteneheptynoic acid.

Preferredly, the compounds of the present invention are "cyclopenteneheptenoic acid derivatives" of the Formula V:

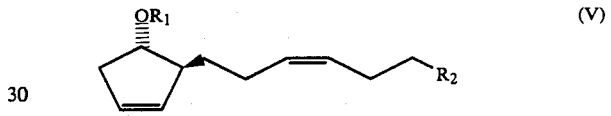
(V)

wherein R$_1$ and R$_2$ are defined as in Formula I.

Representative compounds of the present invention, which are encompassed by Formulas I and V, include, but are not limited to, the following:

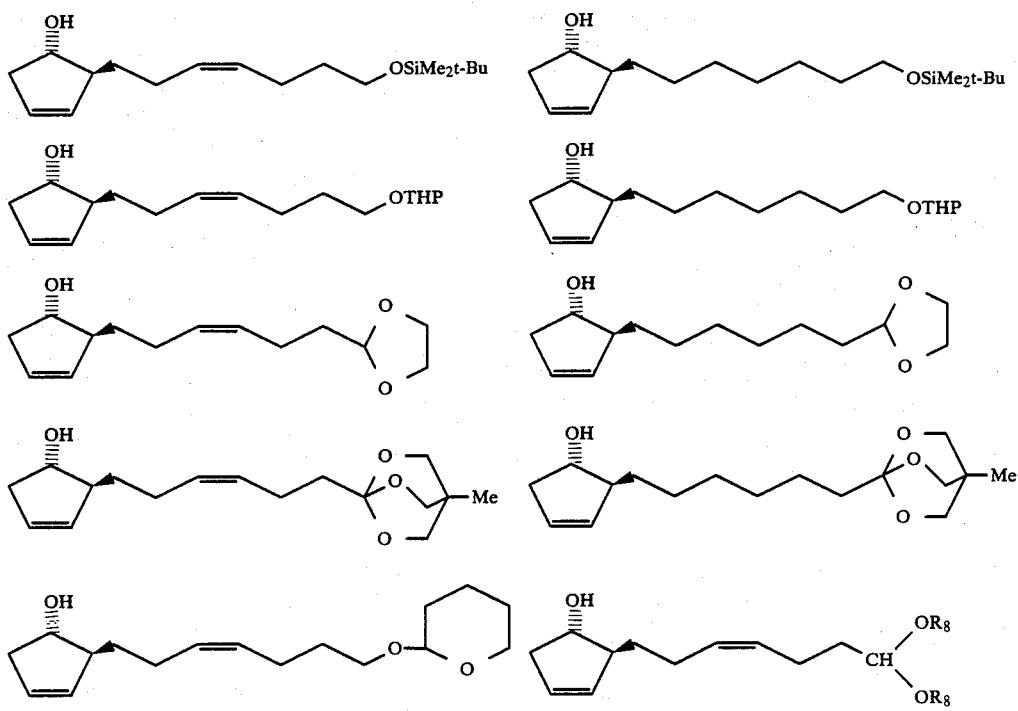

An important characteristic of the compounds of the present invention is that they are chiral and by definition optically active. When these compounds are used as starting materials in the synthesis of prostaglandins the chirality of the compounds of the invention is transferred to the end product resulting in a high yield of optically active prostaglandin. Optical yields of single, chiral isomers of various prostaglandins of 90% and above are possible when the instant compounds are utilized as starting reagents. The following is a description of the preparation of prostaglandins starting with cyclopenteneheptenoic acid derivatives of the present invention.

Once the cyclopenteneheptenoic acid derivative of the invention is formed it may be converted, using well known techniques, to the corresponding cyclopentenone heptenoic acid. A preferred technique for the conversion of the cyclopenteneheptenoic acid derivative to cyclopentenone heptenoic acid derivatives is presented in Example 13 herein, wherein the hydroxyl group on the derivativized cyclopentane ring is oxidized ("Swern Oxidation") by activating dimethyl sulfoxide with an oxidizing agent (i.e., oxalyl chloride) in a non-polar solvent, such as dichloromethane prior to treatment with a tertiary amine base, such as triethylamine, at low temperature, preferably about $-78°$ C. The resultant cyclopentenone compound may then be reacted with a vinyl tin compound of the formula:

$R^3$—CH=CH—Sn($R^2$)$_3$      VI wherein $R^3$—CH=CH— is the omega chain of a natural or synthetic prostaglandin and wherein any hydroxy groups contained in said chain are optimally protected by tri-lower-alkylsilyl. tetrahydropyranyl or tetrahydrofuranyl groups. In Formula VI, each $R^2$ is independently lower alkyl. $R^3$ contains 1 to 10 carbon atoms which may have vinyl or alkynyl unsaturation. Alternatively, $R_3$ may contain cycloalkyl moieties where the cycloalkyl contains 3 to 6 carbon atoms. Further, $R_3$ may be substituted with hydroxy. tri-lower-alkyl-silyloxy, tetrahydropyranyloxy, tetrahydrofuranyloxy, fluoro, or phenoxy. Additionally, $R_3$ may possess these substituents in optically active form. These vinyl tin compounds are made by art recognized techniques. The procedure generally involves the following reaction:

$R^3$—CH=CH—H + H—Sn($R^2{}_3$ → $R^3$—CH=CH—Sn($R^2$)$_3$

U.S. Pat. Nos. 4,499,296; 4,322,543; 4,578,505; and 4,271,314 describe the procedures for making omega side chains for prostaglandins using such thin compounds. Illustrative of such tin compounds are:

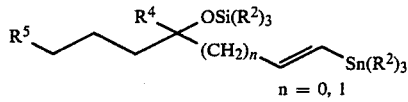
n = 0, 1 wherein $R^4$ is hydrogen or lower alkyl, and $R^2$ is lower alkyl and $R^5$ is lower alkyl containing 1 to 4 carbon atoms, cycloalkyl containing 3 to 6 carbon atoms, cycloalkylalkyl containing 4 to 7 carbon atoms, or cycloalkylalkenyl containing 5 to 7 carbon atoms and wherein n=0, 1.

Specific vinyl stannane compounds, which are useful for forming the higher order cuprate complexes of this invention and for making pharmacologically active prostaglandins, are the following compounds:

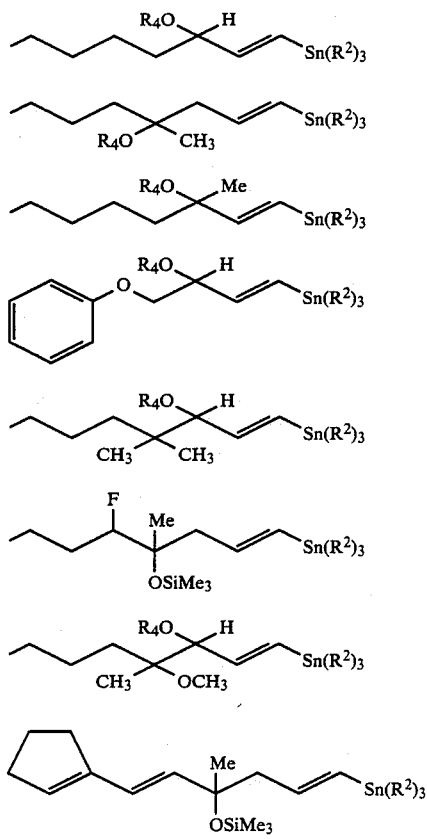

wherein $R^2$ is as defined in the immediately preceding paragraph and R$_4$ is tri-lower-alkylsilyl, tetrahydropyranyl or tetrahydrofuranyl.

The resultant product from a reaction between a cyclopentenone compound, derived from the cyclopenteneheptenoic acid derivatives of the invention, and a vinyl tin compound, as described above, is a prostaglandin. Representative examples of chiral prostaglandins that can be synthesized by starting with the compounds of the instant invention are illustrated in Table I. The preferred reaction mechanism to obtain such prostaglandins is set forth in the example section contained hereinbelow.

TABLE I

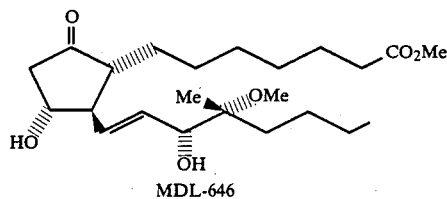

MDL-646

TABLE I-continued

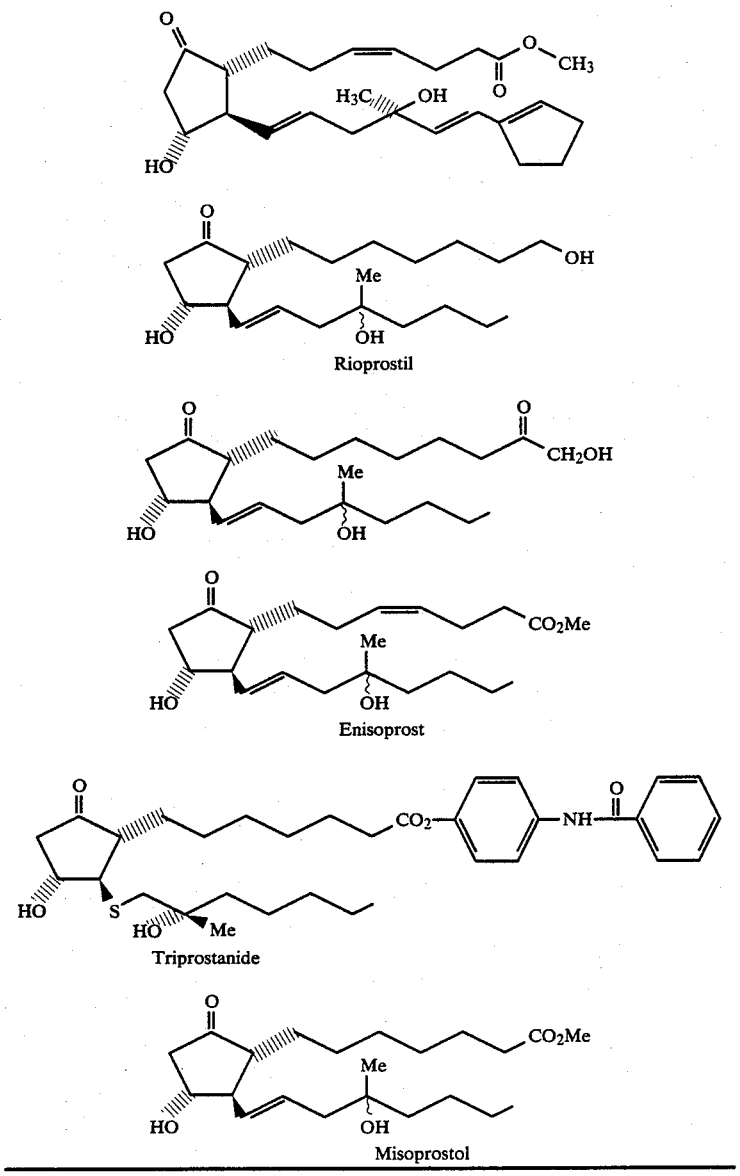

Rioprostil

Enisoprost

Triprostanide

Misoprostol

A preferred method for the preparation of compounds of the present invention involves coupling a higher order cuprate complex with a chiral pentenone precursor. The higher order cuprate complex has the following general formula:

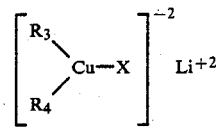

wherein:
(a) X is —CN, —SCN, —OSO$_2$CF$_3$, or —S—phenyl;
(b) R$_3$ is a thienyl; and
(c) R$_4$ is —A—R$_9$ wherein A represents alkylene of from 1 to 8 carbon atoms, alkenylene of from 2 to 8 carbon atoms, or alkynylene of from 2 to 8 carbon atoms;

wherein R$_9$ is

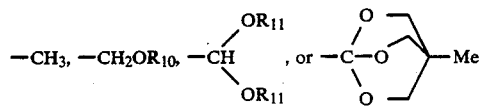

wherein R$_{10}$ is tetrahydropyranyl, ethylvinyl ether, or —Si(R$_{12}$)$_3$;
wherein R$_{11}$ is alkyl, alkylaryl, or —CH$_2$CH$_2$; and
wherein R$_{12}$ is independently alkyl or aryl.

The preferred method employed in the preparation of the higher order cuprate complex is set forth in the example section contained hereinbelow.

Coupled with the higher order cuprate complex to form the compounds of the instant invention is a cyclopentene compound. Specifically, this cyclopentene is a cyclopentenone precursor. What is meant by cyclopentenone precursor is any compound that can be converted by standard chemical reaction techniques to yield a cyclopentenone compound. Additionally, the cyclopentene must be chiral and have at least two chiral centers. Cyclopentenes suitable for use in the invention are those represented by the following general formula:

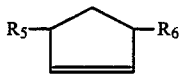

(IV)

wherein $R_5$ and $R_6$ are independently —OH or —OCOR$_7$ with each being bound to a chiral center and where either $R_5$ or $R_6$ is replaced by $R_4$ on the cuprate complex and wherein $R_7$ is —CH$_3$, —C(CH$_3$)$_3$, —phenyl, or —CF$_3$. When the cyclopentene is reacted with the culrate complex either $R_5$ or $R_6$ is replaced by $R_4$ from the cuprate complex of Formula III. Representative examples of cyclopentene compounds useful in practicing the invention include those having the following formula:

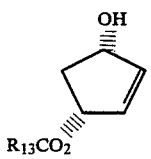

where $R_{13}$ is a lower alkyl or arylalkyl.

The process conditions which facilitate the coupling of the higher order cuprate complex with the cyclopentene include a temperature ranging from −50° to 25° C. Typically the reaction is performed in a suitable solvent, for example, in either an alkyl ether solvent where the alkyl groups have 1 to 6 carbon atoms, or in a cycloalkyl ether solvent having 4 to 6 carbon atoms such as tetrahydrofuran or tetrahydropyrans, or in mixtures of the above ethers with alkane solvents having 5 to 8 carbons. A distinction between the process of the invention and prior art processes is that the prior art teaches coupling of cuprate complexes with cyclopentenone compounds, not chiral cyclopentene compounds. The instant process requires coupling of a cuprate complex with a chiral cyclopentene.

The compounds of the present invention are prepared according to Schemes I–XI herein. Schemes I–III illustrate the synthesis and attachment of the alkyl, alkenyl or alkynyl side chain to the cyclopentene ring. In Scheme I, the —OH moiety of an alcoholic acetylene of Formula X (wherein n is an integer from 2–4, preferably 3) is first protected by reaction with dihydropyran ("DHP") in the presence of an acid catalyst such as H$_2$SO$_4$, to form the corresponding tetrahydropyranyl ("THP") compound XI. The THP protected acetylenic compound XI, having n+2 carbon atoms, is converted to the alcohol XII, having n+4 carbon atoms, by sequential reaction with a strong base, such as n-butyllithlum, in an aprotic solvent, such as tetrahydrofuran, followed by the addition of ethyleneoxide. Upon the addition of the ethylene oxide, the resultant alcohol XII is two carbons longer than the starting acetylenic compound XI. The resultant acetylenic alcohol XII may be converted to the corresponding acetylenic bromide XIII by reaction with carbon tetrabromide ("CBr$_4$") in the presence of triphenylphosphine ("P(Ph)$_3$"). Alternatively, XII may be first reduced to the cis vinyl alcohol XIV by partial hydrogenation over Ni$_3$B$_2$ or it may be converted to the alkyl alcohol XV by complete hydrogenation. Either alcohol XIV or XV is converted to its corresponding bromide XVI or XVII, respectively by reaction with carbon tetrabromide (CBr$_4$) in the presence of triphenylphosphine.

In Scheme II, the alkynyl, alkenyl and alkyl bromo compounds, which correspond to XIII, XVI and XVII respectively, are converted to the corresponding alkynyl, alkenyl and alkyl higher order cuprate compounds XVIII, XIX, and XX respectively. Conversion is accomplished by the sequential reaction of XIII or XVI, or XVII with a strong base, preferably naphthyllithium, in an aprotic solvent such as tetrahydrofuran (THF) followed by the addition of a cooled solution of lithium thienyl copper (I) cyanide which was freshly prepared in THF according to the procedure of Lipshutz, et al., *Tetrahedron Letters*, 28, 945 (1987).

In Scheme III, the higher order cuprate compounds. XVIII, XIX, and XX, having alkynyl, alkenyl, and allyl side chains, respectively, are reacted in an aprotic solvent, preferably tetrahydrofuran, at a low temperature, such as −30° C., with cis-4-cyclopentene-1R,3-diol, 1 acetate XXV, which was prepared according to the method of Deardorf, et al., *Tetrahedron Letters*, 26. 5615 (1985) and 27, 1255 (1986), to produce the corresponding alkynyl XXI, alkenyl XXII, and alkyl XXIII compounds of the present invention.

In Scheme IV, the alkynyl, alkenyl and alkyl cyclopentenyl alcohols corresponding to XXI, XXII and XXIII, respectively, are converted to the alkynyl, alkenyl and alkyl cyclopentenyl acetates corresponding to XXIV, XXV and XXVI, respectively. Conversion is accomplished by the addition of acetic anhydride, triethylamine and a catalytic amount of 4-(N,N-dimethylamino)pyridine to a solution of the alcohol in a nonpolar solvent such as methylene chloride.

In Scheme V, the tetrahydropyranyl ("THP") protecting group is removed from the alkynyl, alkenyl and alkyl cyclopentenyl acetates corresponding to XXIV, XXV and XXVI, respectively, to afford the alcoholic compounds XXVII, XXVIII and XXIX. The deprotection of the THP protected alcohols is performed in a protic solvent, such as isopropanol, with a catalytic amount of pyridinium p-toluene sulfonate.

In Scheme VI, the alkynyl, alkenyl and alkyl alcohols corresponding to XXVII, XXVIII and XXIX, respectively, are oxidized with Jones Reagent in acetone to afford the alkynyl, alkenyl and alkyl cyclopentenyl acids corresponding to XXX, XXXI and XXXII, respectively.

In Scheme VII, the alkynyl, alkenyl and alkyl acids corresponding to XXX, XXXI and XXXII, respectively, are protected as the corresponding 2,2,2-bicyclo orthoesters, XXXIII, XXXIV, and XXXV in a three step reaction. The 2,2,2-bicyclo orthoesters are prepared by first converting the acid to the corresponding acid chloride using thionyl chloride in a solvent, such as benzene. Subsequently, the resultant acid chloride is reacted with 3-methyl-3-oxethane. methanol, followed by rearrangement with a Lewis acid catalyst, such as aluminum chloride, in a solvent such as methylene chloride.

In Scheme VIII, the alcoholic compounds corresponding to XXVII, XXVIII and XXIX, are converted to the corresponding trialkylsilyl protected alcohols XXXVI, XXXVII and XXXVII, respectively. The protection of the alcoholic compounds is accomplished by reacting the appropriate alcohol with a trialkylsilyl-chloride and a base, such as imidazole, in a polar solvent such as dimethylformamide. By "alkyl" as used in trialkylsilyl is meant straight or branched chain alkyl having from 1-6 carbon atoms. In Scheme VIII, the trialkylsilyl chloride is dimethyl t-butylsilyl chloride or "$(CH_3)_2t\text{-}C_4H_9SiCl$" (hereinafter $Me_2t\text{-butylSiCl}$).

In Scheme IX, the alcoholic alkynyl, alkenyl and alkyl compounds corresponding to XXVII, XXVIII and XXIX, respectively, are oxidized to the corresponding alkynyl, alkenyl and alkyl aldehydes corresponding to XXXIX, XL and XLI, respectively, using Sarett's Reagent ($CrO_3\text{---}(C_5H_5N)_2$) in a polar solvent such as methylene chloride.

In Scheme X, the aldehyde moieties of the alkynyl, alkenyl and alkyl compounds corresponding to XXXIX, XL and XLI, respectively, are protected as 1,3-dioxolanes. The protection is accomplished by stirring the respective aldehydes with ethylene glycol in the presence of an acid catalyst, such as $H_2SO_4$, and results in the alkynyl, alkenyl and alkyl compounds corresponding to XLII, XLIII and XLIV, respectively.

Alternatively, in Scheme XI, the alkynyl, alkenyl and alkyl aldehydic compounds corresponding to XXXIX, XL and XLI, respectively, are protected as the alkynyl, alkenyl and alkyl acetals corresponding to XLV, XLVI and XLVII, respectively, by stirring the appropriate aldehyde with methanol in the presence of an acid catalyst such as $H_2SO_4$.

-continued
Scheme II

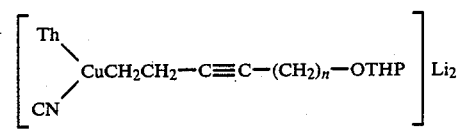

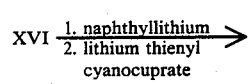

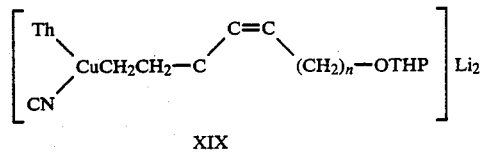

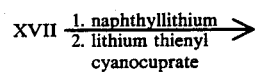

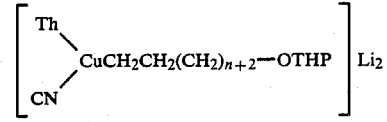

Scheme 1

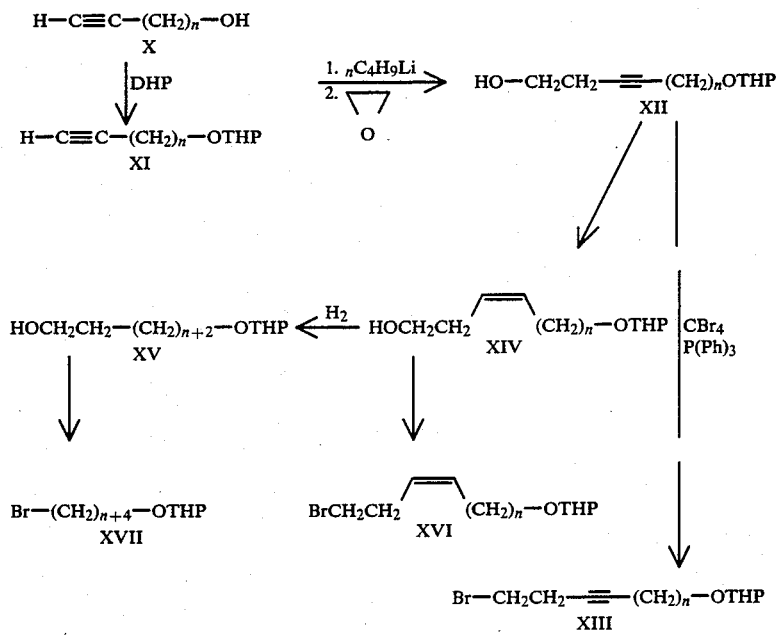

Scheme III

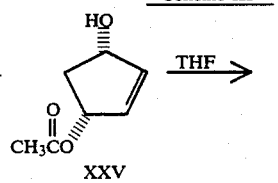

Scheme II

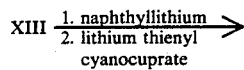

4,952,710
13
-continued
Scheme III
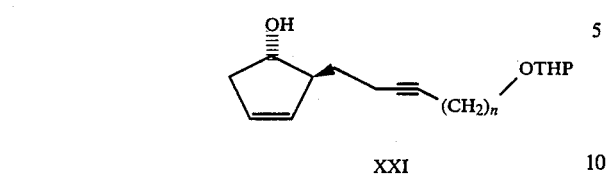
XXI
XIX + 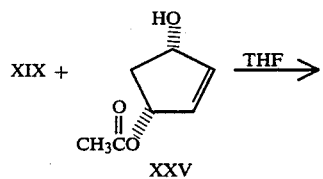 $\xrightarrow{\text{THF}}$
XXV
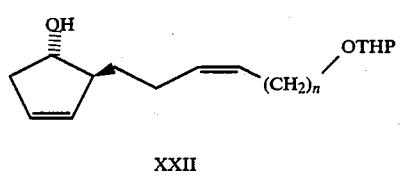
XXII
XX + 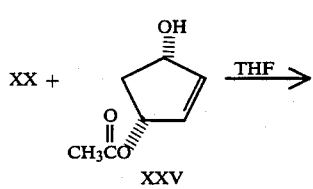 $\xrightarrow{\text{THF}}$
XXV
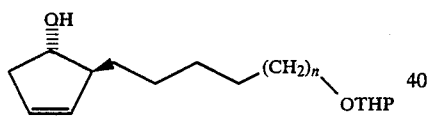
XXIII
Scheme IV
XXI 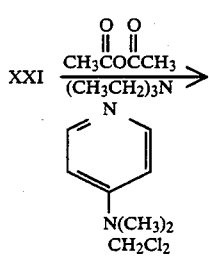 →
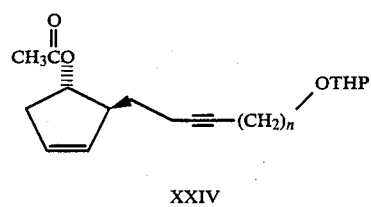
XXIV
14
-continued
Scheme IV
XXII 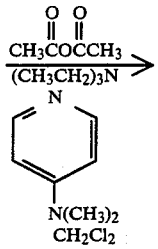 →
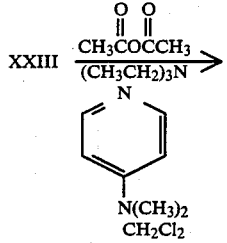
XXV
XXIII 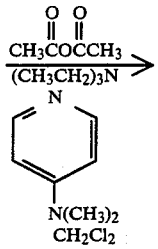 →
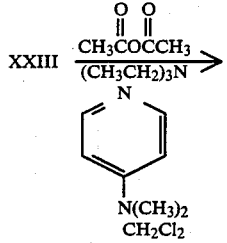
XXVI
Scheme V
XXIV 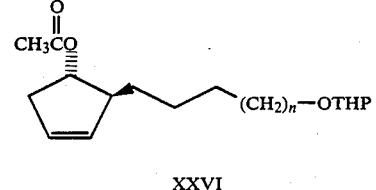 →
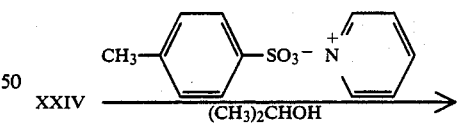
XXVII
XXV 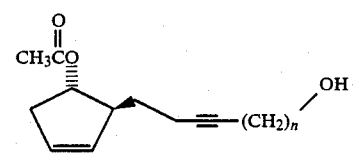 →

Scheme V

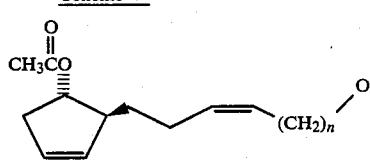
XXVIII

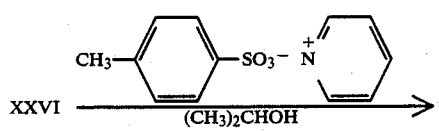

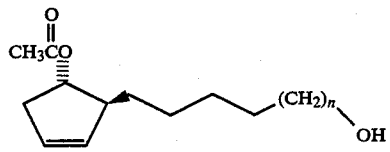
XXIX

Scheme VI

XXVII $\xrightarrow{\text{Jones Reagent (CrO}_3\text{, dilute H}_2\text{SO}_4\text{)}}{\text{Acetone}}$

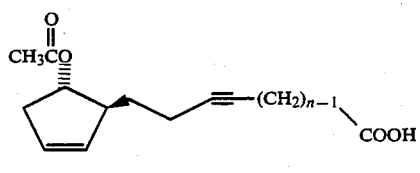
XXX

XXVIII $\xrightarrow{\text{Jones Reagent (CrO}_3\text{, dilute H}_2\text{SO}_4\text{)}}{\text{Acetone}}$

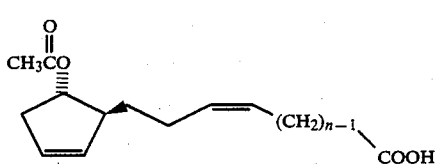
XXXI

XXIX $\xrightarrow{\text{Jones Reagent (CrO}_3\text{, dilute H}_2\text{SO}_4\text{)}}{\text{Acetone}}$

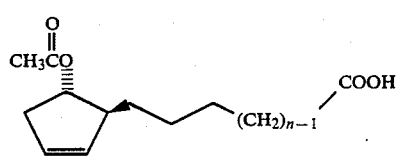
XXXII

Scheme VII

XXX $\xrightarrow[\text{3. AlCl}_3/\text{CH}_2\text{OH}]{\substack{1.\ \text{SOCl}_2/\text{C}_6\text{H}_6 \\ 2.\ \text{see structure}}}$

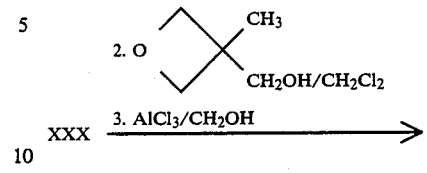

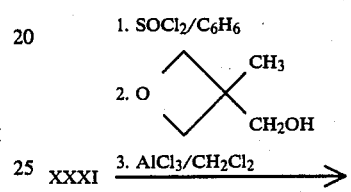
XXXIII

XXXI $\xrightarrow[\text{3. AlCl}_3/\text{CH}_2\text{Cl}_2]{\substack{1.\ \text{SOCl}_2/\text{C}_6\text{H}_6 \\ 2.\ \text{see structure}}}$

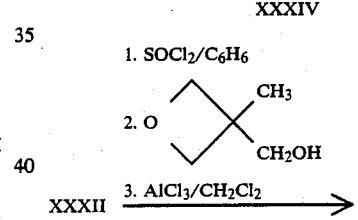
XXXIV

XXXII $\xrightarrow[\text{3. AlCl}_3/\text{CH}_2\text{Cl}_2]{\substack{1.\ \text{SOCl}_2/\text{C}_6\text{H}_6 \\ 2.\ \text{see structure}}}$

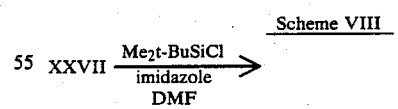
XXXV

Scheme VIII

XXVII $\xrightarrow[\text{DMF}]{\text{Me}_2t\text{-BuSiCl, imidazole}}$

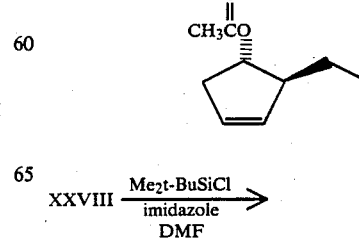
XXXVI

XXVIII $\xrightarrow[\text{DMF}]{\text{Me}_2t\text{-BuSiCl, imidazole}}$

-continued
Scheme VIII

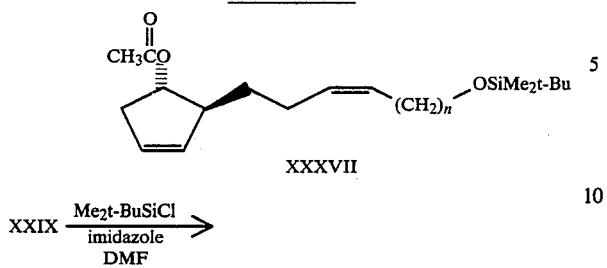

XXIX $\xrightarrow[\text{DMF}]{\text{Me}_2\text{t-BuSiCl}\atop\text{imidazole}}$

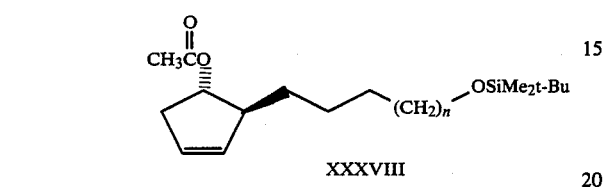

Scheme IX

XXVII $\xrightarrow[\text{CH}_2\text{Cl}_2]{\text{CrO}_3.(\text{C}_5\text{H}_5\text{N})_2}$

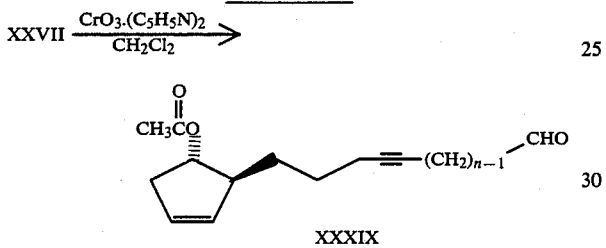

XXVIII $\xrightarrow[\text{CH}_2\text{Cl}_2]{\text{CrO}_3.(\text{C}_5\text{H}_5\text{N})_2}$

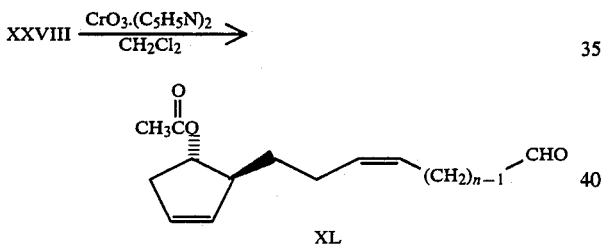

XXIX $\xrightarrow[\text{CH}_2\text{Cl}_2]{\text{CrO}_3.(\text{C}_5\text{H}_5\text{N})_2}$

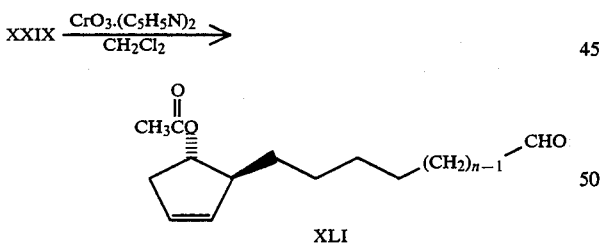

Scheme X

XXXIX $\xrightarrow[\text{(cat) H}_2\text{SO}_4]{\text{HOCH}_2\text{CH}_2\text{OH}}$

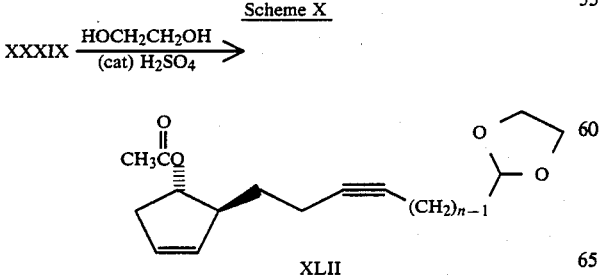

XL $\xrightarrow[\text{(cat) H}_2\text{SO}_4]{\text{HOCH}_2\text{CH}_2\text{OH}}$ -continued
Scheme X

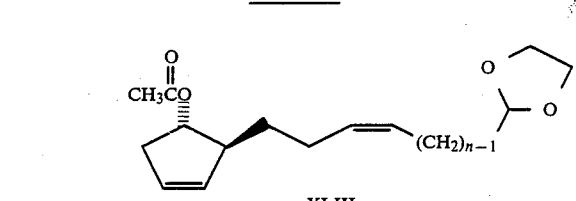

XLI $\xrightarrow[\text{(cat) H}_2\text{SO}_4]{\text{HOCH}_2\text{CH}_2\text{OH}}$

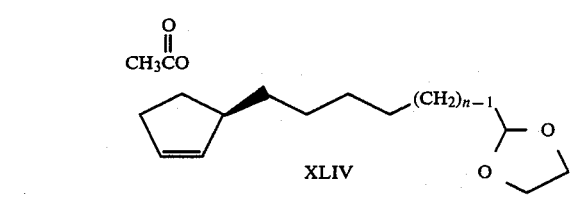

Scheme XI

XXXIX $\xrightarrow[\text{(cat) H}_2\text{SO}_4]{\text{CH}_3\text{OH}}$

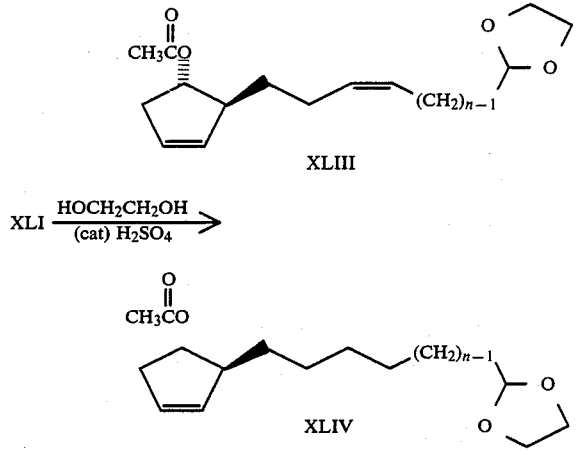

XL $\xrightarrow[\text{(cat) H}_2\text{SO}_4]{\text{CH}_3\text{OH}}$

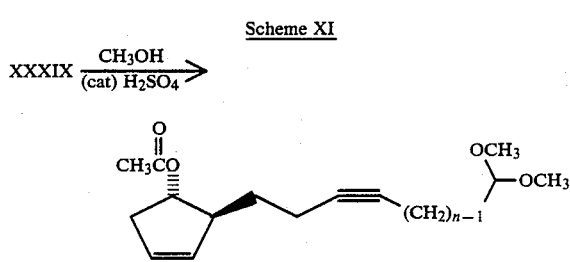

XLI $\xrightarrow[\text{(cat) H}_2\text{SO}_4]{\text{CH}_3\text{OH}}$

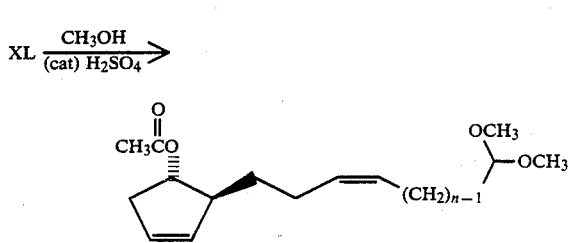

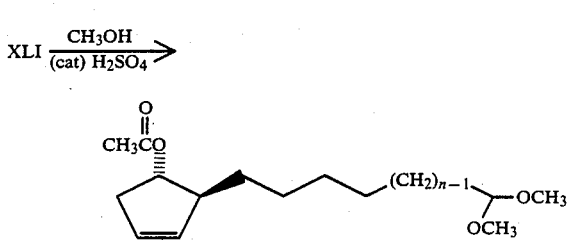

DESCRIPTION OF THE PREFERRED EMBODIMENTS

The following examples further illustrate details of the preparation of the compounds of this invention. The invention, which is set forth in the foregoing disclosure, is not to be construed or limited either in spirit or in scope of these examples. Those skilled in the art will readily understand that known variations of the conditions or processes of the following preparative procedures can be used to prepare these compounds. All temperatures are degree celsius unless otherwise noted, the numbers in the parentheses correspond to the number shown in the reaction scheme below. "R" is tetrahydropyranyl and "Th" is thienyl.
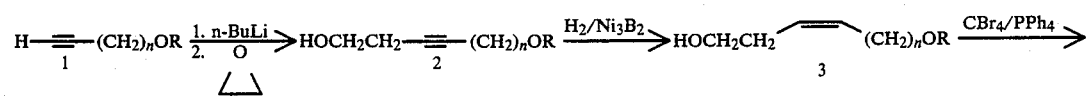
R = THP
n = 3
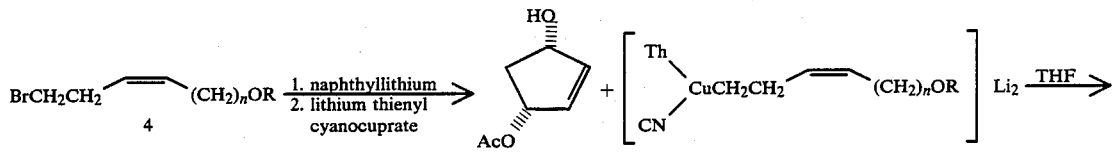
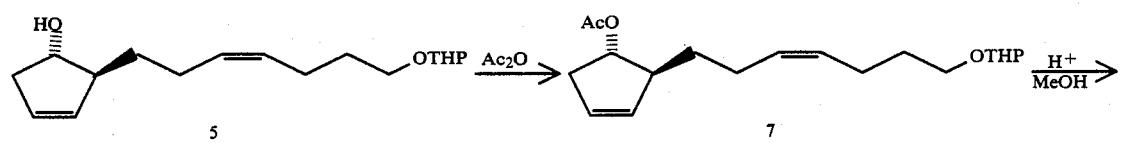
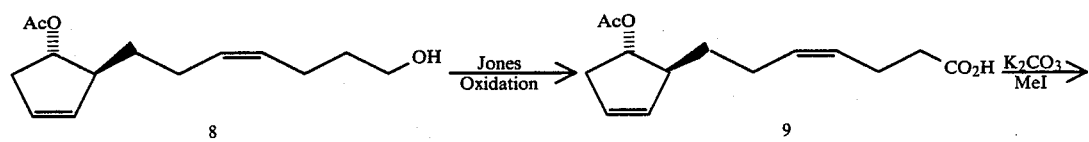
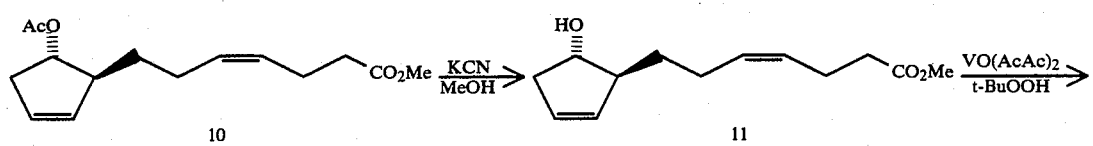
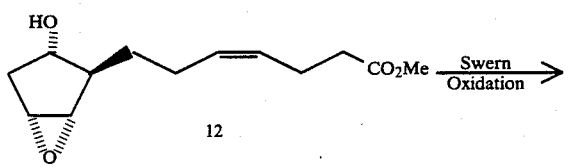
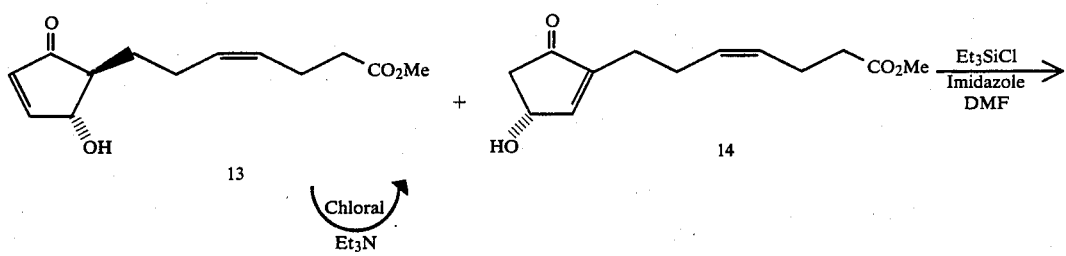
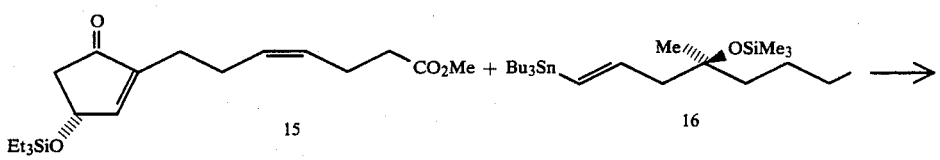
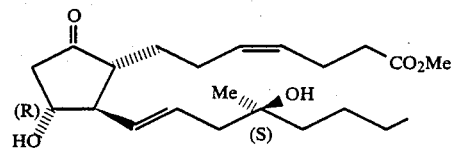

-continued

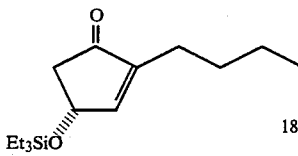 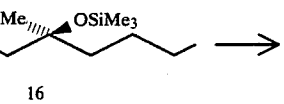 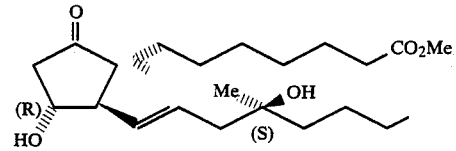

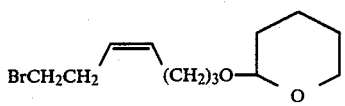

EXAMPLE I

The preparation of
7-[(tetrahydro-2H-pyran-2-yl)oxy]-3-heptyn-1-ol (2).

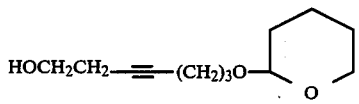

To a cooled solution (−20° C.) of tetrahydro- 2-(4-pentynyloxy)-2H-pyran (1) (16.8 g. 0.10 mole) and tetramethylethylene diamine (45.2 mL, 0.30 mole, distilled from CaH₂ under nitrogen) in anhydrous tetrahydrofuran (100 mL. distilled from sodium/benzophenone under nitrogen) was added via syringe a solution of n-butyllithium (41.0 mL, 0.101 mole, 2.44 N in hexane). The mixture was allowed to warm to 0° C. over 30 minutes and stirred at 0° C. for 1 h followed by the addition, via cannula, of ethylene oxide (8 8 g, 0.20 mole, freshly condensed into an argon filled graduated cylinder). The solution was stirred at 0° C. for 1 h and then stored in a refrigerator (5° C.) for 3 days. The reaction mixture was poured into water (200 mL) and extracted with ether (1×200 mL, 2×50 mL). The organic layers were combined and washed with water (5×50 mL), saturated sodium chloride (50 mL), dried (MgSO₄), and concentrated to provide 22.80 g of a crude amber oil which was chromatographed (ethyl acetate/hexane 1:1) to provide 12.09 g (59%) of the title compound: R$_f$=0.32 (ethyl acetate/hexane:1/1) ¹H PMR (CDCl₃); δ 4.60 (t, J=3 Hz, 1H), 3.85 (m, 2H), 3.67 (t, J=6 Hz, 2H), 3.50 (m, 2H), 2.71 (bs, 1H), 2.40 (m, 4H), 2.29 (m, 2H), 1.78 (m, 4H), 1.52 (m, 4H); ¹³C NMR (CDCl₃): 98.9, 81.5, 77.1, 65.9, 62.2, 61.3, 30.7, 29.0, 25.5, 23.1, 19.5, 15.7 ppm; IR (CHCl₃): 3600, 3460 cm⁻¹; Analysis calculated for C₁₃H₂₀O₃: C, 67.89; H, 9.50; Found: C, 67.96; H, 9 79.

EXAMPLE 2

The preparation of
7-[(tetrahydro-2H-pyran-2-yl)oxy]-3Z-hepten- 1-ol (3).

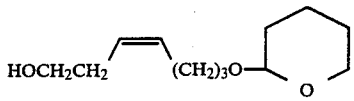

To a nitrogen flushed Parr bottle (500 mL) was added, with stirring, a solution of nickel acetate(H₂O)₄ (2.19 g, 8.83 mmol) in methanol (70 mL) followed by the slow addition of a uolution of ethylenediamine (2.35 mL. 35.2 mmol), H₂O (10.0 mmol), and sodium borohydride (0.39 g, 10.2 mmol) in methanol (32 mL). After stirring at 25° C. for 5 min, to this preformed suspension of black nickel boride was added a solution of the product of Example 1 (18.69 g, 88.2 mmol) in methanol (170 mL). The Parr bottle reactor was then placed on a Parr shaker and flushed with nitrogen followed by exposure to hydrogen at 64 psi. The progress of the reaction was monitored by hydrogen uptake and terminated after hydrogen uptake had ceased (at 95% of theory, approx. 2h). The reactor was vented, purged with nitrogen and opened. The contents of the flask were filtered through celite followed by a rinse of methanol (100 mL). The combined purple colored filtrates were concentrated to provide a thick oil which was partitioned between water (100 mL) and ethyl acetate 200 mL). The aqueous layer was reextracted with ethyl acetate (2×50 mL). The organic layers were combined, washed with water (2×50 mL), saturated sodium chloride (50 mL), dried (MgSOhd 4), and concentrated to provide 18.72 g (100%) of the title compound as a pale yellow oil: R$_f$=0.32 (ethyl acetate/hexane:1/1); ¹H PMR (CDCl₃): δ 5.6–5.3 (m, 2H), 4.56 (t, J=4 Hz, 1H), 3.87 (m, 1H), 3.75 (m, 1H), 3.61 (m, 2H), 3.50 (m, 1H), 3.40 (m, 1H), 2.32 (broad q, J=b 8 Hz, 2H), 2.18 (broad q, J=8 Hz, 2H), 1 9–1.3 (m, 6H); ¹³C NMR (CDCl₃): 132.1, 126.1, 99.0, 66.8, 62.5, 62.2, 30.8, 29.6, 25.5, 24.0, 19.7 ppm; IR (CHCl₃): 3600, 3440, 3000, 1030 cm⁻¹; Exact mass calculated for C₁₂H₂₂O₃: 214.1596; Found 214.1569.

EXAMPLE 3

The preparation of
2-[(7-bromo-4Z-heptenyl)oxy]-tetrahydro-2H-pyran (4).

To a vigorously stirred cold (−42° C.) solution of the product of Example 2 (72.8 g, 0.34 mole), carbon tetrabromide (134.7 g, 0.40 mole) and dry dichloromethane (600 mL, distilled from phosphorous pentoxide under argon) was added, portionwise over 30 min, triphenylphosphine (96.9 g, 0.37 mole). The temperature was maintained below −38° C. during the addition and then the reaction mixture was allowed to warm to 25° C. (approx., 2h). The solvent was concentrated and the resultant viscous oil was triturated with hexane (1 L), cooled to −78° C. for 1 h and then filtered through celite. The filter cake was washed with cold hexane (200 mL) and the combined organics were concentrated. The oil was triturated again, as described above, and concentrated to give 157.8 g of a pale yellow oil which was chromatographed (hexane/ethyl acetate:95/5) to provide 77.8 g (83% yield) of the title compound as a colorless oil: $R_f=0.37$ (hexane/ethyl acetate:93/7); $^1$H PMR (CDCl$_3$) δ 5.6–5.3 (m, 2H), 4.58 (t, 1H), 3.9–3.3 (m, 4H), 2.62 (q, 2H), 2.15 (q, 2H), 1.9–1.4 (m, ?H); $^{13}$C NMR (CDCl$_3$): 132.3, 126.4, 98.9, 66.7, 62.4, 32.5, 30.8, 30.7, 29.5, 25.5, 24.1, 19.8; IR (CHCl$_3$): 3000, 1430, 1265 cm$^{-1}$; Exact mass calculated for C$_{12}$H$_{21}$O$_2$Br: 276.0747; Found: 276.0725.

EXAMPLE 4

Lithium Alkyl Thienyl Copper Cyanide Higher Order Cuprate Preparation.

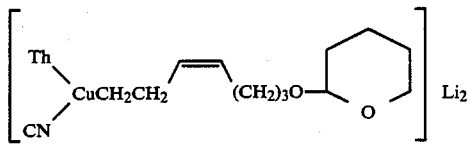

Lithium thienyl copper(I) cyanide was prepared according to the method of B. Lipshutz, et al., *Tetrahedran Letters*, 1987, 28, 945. To a cooled (−30° C.) tetrahydrofuran (100 mL) solution of thiophene (freshly distilled, 15.96 g, 15.2 mL, 0.19 mole) was added n-butyllithium (2.4 M in hexane, 79.2 mL, 0.19 mole) dropwise, via syringe, at a rate such that the temperature did not exceed −17° C. The homogenous mixture was was stirred at −25° C. for 5 min, warmed to 0° C. for 30 min and then recooled to −25° C. This solution was then added via cannula to a vigorously stirred suspension of copper(I) cyanide (16.91 g, 0.19 mole) in cooled (−25° C.) tetrahydrofuran (120 mL) at such a rate that the temperature did not exceed −20° C. The initial hsterogenous mixture was stirred at .25° C. for 1.5 h during which time all the solids dissolved resulting in a deep amber colored homogeneous solution of lithium thienyl copper(I) cyanide.

The required alkyl lithium was prepared using naphthyl lithium as follows. To a 2 L three necked flask, equipped with a pressure equalized addition funnel and a mechanical stirrer, was added tetrahydrofuran (450 mL) followed by naphthyl lithium (0.5 M in tetrahydrofuran, 750 mL, 0.375 mole). The diluted naphthyl lithium solution was stirred vigorously and cooled to −75° C. A cold (−75° C.) solution of the product from Example 3 (51.97 g, 0.189 mole) in tetrahydrofuran (100 mL) was then added, via cannula, at such a rate that the internal temperature did not exceed −65° C. (addition time approx. 1 hour). This mixture was stirred at −78° C. for 30 min and then the freshly prepared solution of lithium thienyl copper(I) cyanide (cooled to −25° C.) was added via cannula. The resulting higher order cuprate, lithium alkyl thienyl copper(I) cyanide, was stirred at −78° C. for 5 min and then warmed to −30° C. for 30 min.

EXAMPLE 5

Preparation of 2β-[[7-(tetrahydro-2H-pyran-2-yl)oxy]-3-Z-heptenyl]-3-cyclopenten-1S,1α-ol (5).

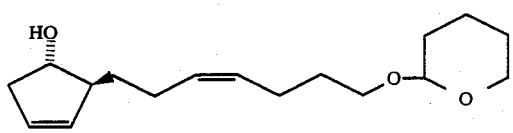

To a cooled (−30° C.) solution of lithium alkyl thienyl copper(I) cyanide (0.19 moles, 0.11 M in tetrahydrofuran), prepared as described in Example 4, was added, via syringe, a solution of cis-4-cyclopentene-1R, b 3-diol, 1-acetate (11.93 g, 0.084 mole), prepared according to the method of Deardorf, et al., *Tetrahedron Letters*, 1985, 26, 5615, and 1986, 27, 1255), in tetrahydrofuran (30 mL). The resulting solution was stirred at −30° C. for 3 h followed by gradual warming to 10° C. over approx. 3 h. The reaction was quenched by adding a 10% solution of concentrated ammonium hydroxide in saturated ammonium chloride (650 mL) to the vigorously stirred mixture followed by flushing the reaction flask with air for 1 h. The deep blue aqueous layer was separated and extracted with ether (200 mL). The organic layers were combined, washed with a 10% solution of concentrated ammonium hydroxide in saturated ammonium chlcride (3×75 mL, throughout the third washing the aqueous layer remained colorless), washed with saturated sodium chloride (75 mL), dried (MgSO$_4$), and concentrated to provide an oil which contained solid naphthalene. The naphthalene was removed by bulb-to-bulb distillation (72° C. at 0.2 mm Hg) and the amber oily residue from the distillation was purified by medium pressure chromatography (hexane/ethyl acetate:7/3) providing 21.31 g of the title compound (91% yield): $R_f=0.46$ (hexane/ethyl acetate:1/1); $^1$H NMR (CDCl$_3$): δ 5.68 (m, 2H), 5.39 (m, 2H), 4.58 (t, 1 H), 4.09 (bs, 1H), 3.86 (m, 1H), 3.74 (m, 1H), 3.50 (m, 1H), 3.39 (m, 1H), 2.68 (dm, J=2, 17 Hz, 1H), 2.60 (bs, 1H), 2.51 (m, 14H), 2.24 (dm, J=2, 17 Hz, 1H), 1.9–1 2 (m, 10H); $^{13}$C NMR (CDCl$_3$): 133.1, 130.1, 129.5, 128.0, 98.9, 77.4, 67.0, 62.3, 54.6, 41.7, 33.3, 30.8, 30.0, 25.6, 25.5. 24.0, 19.7 ppm; IR(CHCl$_3$): 3500, 3010, 1030 cm$^{-1}$. Analysis calculated for C$_{17}$H$_{28}$O$_3$: C, 72.81; H, 10.06. Found: C, 72.78; H, 10.18.

EXAMPLE 6

Preparation of 2β-[7-[(tetrahydro-2H -pyran- 2-yl) oxy]-3Z-heptenyl]-3-cyclopenten-1S,1α-yl α-methoxy-α-(trifluoromethyl)-benzeneacetate, the Mosher's ester of compound of Example 5.

To a solution of the cuprate adduct of Example 5 (28 mg. 0.1 mmol) and dry pyridine (40.0 mg, 0.50 mmol) in anhydrous methylene chloride (1.5 mL, distilled from phosphorou: pentoxide under nitrogen) was added, via syringe, a solution of (R)-(+)-α-methoxy-α-(trifluoromethyl)phenylacetic acid chloride (prepared from the commercially available acid by reaction with thionyl chloride) in anhydrous metlylene chloride (1.0 mL). The mixture was allowed to stand at 25° C. overnight and then was partitioned between saturated sodium chloride (25 mL) and ethyl acetate (75 mL). The organic layer was washed with saturated sodium chloride (10 mL), dried (MgSO$_4$), concentrated, and purified by PrepTLC (silica, hexane/ethyl acetate:8/2) to provide the title compound: Rf=0.44 (by comparison with racemic material it was determined that no optical enrichment occurred during chromatography). The optical purity of the compound of Example 5 was determined by $^1$H NMR in CDCl$_3$ of the corresponding Mosher's ester. The intergration of two discernible sets of multiplets at δ 2.90 and 2.41 was indicative of the optical purity. This material was compared to the 1 1 mixture of diastereomers resulting from Mosher ester formation using the racemic compound of Example 5 prepared in an identical manner as the chiral title compound. The $^1$H NMR of this 1:1 mixture of diastereomers displayed four sets of multiplets with equal intergrations at δ 2.90, 2.85, 2.7, and 2.41. By comparing the intergration of these signals in the $^1$H spectra of the optically active title compound, it was determined that the desired diastereomer was present in greater than or equal to 97%. This represents ar enantiomeric excess of greater than or equal to 94% for the compound of Example 5.

EXAMPLE 7

Preparation of 2β-[[7-(tetrahydro-2H-pyran-2-yl)oxy]-3Z-heptenyl]-3-cyclopenten-1S, 1α-ol, 1-acetate (7).

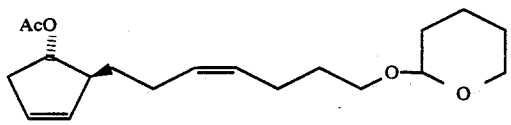

To a cooled (5–10° C.) solution of the compound of Example 5 (41.76 g, 0.149 mole) in methylene chloride (200 mL, distilled from phosphorous pentoxide under argon) was added dry triethylamine (40.4 g, 55.3 mL, 0.40 mole, freshly distilled from CaH$_2$), 4-(N,N,dimethyl-amino)pyridine (122 mg, 1.0 mmole), followed by the dropwise addition, via syringe, of acetic anhydride (30.6 g, 28.3 mL, 0.30 mole). An ice bath was applied to the reaction mixture to maintain the temperature at or below 10° C. during the addition. The mixture was stirred a 0° C. for 1 h and then at 25° C. overnight TLC (hexane/ethyl acetate:10/1) indicated the reaction was complete. The mixture was then diluted with ether (500 mL), treated with saturated sodium bicarbonate (300 mL) plus solid sodium bicarbonate (20 g), and stirred vigorously for 1 h. The aqueous layer was separated and washed with ether (100 mL). The organic layers were combined, washed with saturated sodium bicarbonate (50 mL), saturated sodium chloride (50 mL), dried (MgSO$_4$), filtered, concentrated at reduced pressure, and chromatographed (hexane/ethyl acetate:93/7) to provide 44.86 g (93% yield) of the title compound as a colorless oil: R$_f$=0.32 (hexane/ethyl acetate: 9/1); $^1$H NMR (CDCl$_3$): δ 5.70 (m, 1H), 5.39 (m, 1H), 5.01 (dt. 1H), 4.58 (m, 1H), 3.87 (m, 1H), 3.50 (m, 1H), 3.75 (dt, 1H), 3.49 (dt, 1H), 2.80 (m, 1H), 2.69 (m, 1H), 2.28 (m, 1H). 2.09 (s, 3H), 2.1 (m, 4H), 1.9–1.3 (m, 8H); $^{13}$C NMR (CDCl$_3$): 170.8, 132.7, 129.6, 129.5, 127.8, 98.7, 79.2, 66.8, 62.2, 51.5, 38.9, 32.9, 30.7, 29.6, 25.4, 25.0, 23.8, 21.2, 19.6 ppm; IR(CHCl$_3$): 1725 cm$^{-1}$; Exact mass calculated for C$_{17}$H$_{26}$O$_2$ (M−HOAc): 262.1933; Found 262.1964.

EXAMPLE 8

Preparation of 2 β-(7-hydroxy-3Z-heptenyl)-3-cyclopenten-1S,1 α-ol, 1-acetate (8).

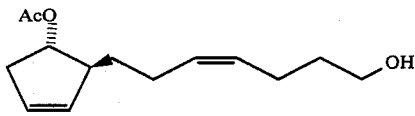

To a nitrogen flushed solution of the chiral acetate of Example 7 (44.0 g, 0.137 mole) in isopropanol (500 mL) was added pyridinium p-toluenesulfonate (500 mg, 0.002 mole). The resulting solution was heated (60° C.) with stirring until TLC (hexsne/ethyl acetate:4/1) analysis indicated the reaction was complete (approx. 20 h). The mixture was cooled. concentrated and chromatographed (hexane/ethyl acetate: 9/1) to provide 29.47 g (91% yield) of the title compound as a colorless oil: R$_f$=0.20 (hexane/ethyl acetate:4/1); $^1$H NMR (CDCl$_3$) δ 5.70 (m, 1H), 5.39 (m, 1H), 5.02 (dt, 1H), 3.62 (m, 2H), 2.80 (m, 1H), 2.69 (m, 1H), 2.60 (m, 1H), 2.29 (m, 1H), 2.11 (m, 4H) 2.02 (s, 3H) 1.7–1.3 (m, 4H); $^{13}$C NMR (CDCl$_3$) 172.0, 133.6, 130.6, 130.4, 128.6, 80.1, 62.9, 52.5, 39.7, 33.7, 33.6, 25.9, 24.4, 22.1 ppm; IR(CHCl$_3$) 3620, 3500, 1725 cm$^{-1}$; Exact mass calculated for C$_{14}$H$_{22}$O$_3$: 238.1587; Found: 238.1569.

EXAMPLE 9

Preparation of 7-[5β-(acetyloxy)-2-cyclopenten-1S,1α-yl]-4Z-heptenoic acid (9).

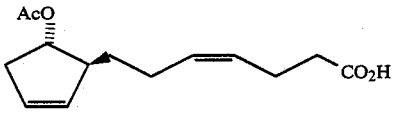

In a three necked flask (500mL) equipped with a mechanical stirrer, pressure equalized addition funnel and an ice bath, a solution of freshly prepared Jones reagent (53 mL, 424 meq., 8N) was added to acetone (200 mL). To this cooled (0° C.) vigorously stirred mixture was added, dropwise over 5 minutes, a solution of the alcohol of Example 8 (20.2 g, 84.9 mmol) in acetone (35 mL). Stirring was continued for 20 min. at 0° C. providing a blue green precipitate. The mixture was diluted with ether (300 mL), stirred for 5 min., filtered through celite (filter cake washed with ether, 100 mL), and concentrated to provide a blue-green oil which was redissolved in ethyl acetate and washed with water (2×50 mL), saturated sodium chloride (50 mL), dried (MgSO$_4$) and concentrated to provide 19.05 g of an oil (89% yield). This material was carried on without purification. An aliquot was purified by medium pressure chromatography (chloroform/ethanol:9/1) to provide the title compound as a colorless oil: R$_f$=0.25 (silica, chloroform/ethanol:9/1); $^1$H NMR (CDCl$_3$); δ 5.70 (m, 1H), 5.40 (m, 1H), 5.02 (dt, 1H), 2.80 (dm, 1H), 2.69 (m, 1H), 2.39 (m, 2H); 2.29 (dm, J=18 Hz, 1H), 2.11 (q, J=18 Hz, 4H), 2.03 (s, 3H), 1.6–1.3 (m, 2H); $^{13}$C (CDCl$_3$): 179.4, 171.7, 133.0, 131.2, 128.2, 127.8, 79.7, 51.9, 39.2, 34.2, 33.1, 25.3, 22.8, 21.6 ppm; IR (CHCl$_3$) 3500−2400, 1710 cm$^{-1}$; Exact mass calculated for C$_{12}$H$_{16}$O$_2$ (M-HOAc): 192.1174; Found: 192.1150.

EXAMPLE 10

Preparation of methyl 7-[5β-(acetyloxy)-2-cyclopenten-1S-1α-yl]-4Z-heptenoate (10).

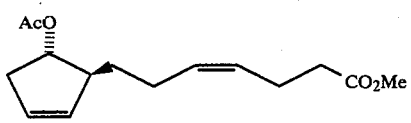

To a flask equipped with a magnetic stirrer and a drying tube containing calcium carbonate, was added potassium carbonate (12.93 g, 93.0 mmol) followed by the carboxylic acid of Example 9 (23.43 g, 93.0 mmol) in dimethylformamide (dried over 4A molecular sieves, 50 mL). To this vigorously stirred mixture was added methyl iodide (28.4 g, 12.5 mL, 0.2 mole). The mixture was stirred overnight and then poured into water (250 mL) and extracted with ether (1×200 mL, 2×100 mL). The ether extracts were combined, washed with water (2×50 mL), saturated sodium chloride (25 mL), dried (MgSO$_4$), and concentrated to provide 23.67 g (96% yield) of an amber oil which was carried on without purification. A small sample was purified by medium pressure chromatography (gradient elution from hexane/ethyl acetate:93/7 to hexane/ethyl acetate 85/15) providing the title compound as a colorless oil: R$_f$=0.30 (hexane/ethyl acetate:4/1); $^1$H PMR (CDCl$_3$): δ 5.70 (m, 1H), 5.40 (m, 2H), 5.02 (dt, J=3 and 7 Hz, 1H), 3.68 (s, 3H), 2.80 (dm, 1H), 2.69 (m, 1H), 2.38 (m, 2H), 2.30 (dm, 1H), 2.11 (dq, 2H), 2.03 (s, 3H), 1.6–1.3 (bm, 2H); $^{13}$C (CDCl$_3$); 173.7, 171.1, 132.9, 130.9, 128.1, 128.0, 79.4, 51.8, 51.7, 39.1, 34.2, 33.0, 25.2, 22.9, 21.5 ppm; Exact mass calculated for C$_{13}$H$_{18}$ O$_2$ (M-HOAc): 206.1306; Found: 206.1307.

EXAMPLE 11

Preparation of methyl 7-[5β-hydroxy-2-cyclopenten-1S,1α-yl]-4Z-heptenoate (11).

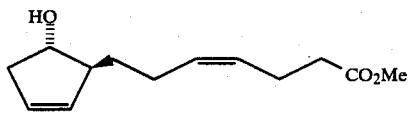

To a solution of the compound of Example 10 (28.30 g, 0.106 mole) in anhydrous methanol (100 mL, distilled from magnesium metal) was added a catalytic amount of potassium cyanide (135 mg, 2.0 mmol). This solution was stirred at 50°–55° C. until the reaction was complete (TLC, hexane/ethyl acetate:1/1, approx. 20h). The solvent was concentrated to provide a thick oil which was dissolved in ether, washed with water (3×25 mL), saturated sodium chloride (25 mL), dried (MgSO$_4$), concentrated and chromatographed (hexane/ethyl acetate:7/3) to provide 15.87 g (67% yield based on the compound of Example 8) of the title compound as a colorless oil: R$_f$=0.30 (hexane/ethyl acetate:1/1), $^1$H NMR (CDCl$_3$): δ 5.69 (m, 1H), 5.4 (m, 1H), 4.10 (bm, 1H), 3.67 (s, 3H), 2.70 (dm, 1H), 2.52 (m, 1H), 2.38 (m, 2H); $^{13}$C NMR (CDCl$_3$): 173.8, 133.0, 131.0, 127.9, 127.8, 77.2, 54.5, 51.6, 41.6, 34.0, 33.0, 25.4. 22.8 ppm; IR(CHCl$_3$): 3600, 3500, 1730 cm$^{-1}$; Exact mass calculated for C$_{13}$H$_{20}$O$_3$: 224.1429; Found: 224.1412.

EXAMPLE 12

Preparation of methyl 7-[3β-hydroxy-1S,1α,5α-6-oxabicyzlo [3.1.0]hex-2α-yl]-4Z-heptenoate (12).

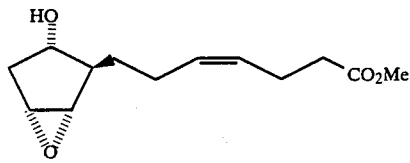

To a cooled (0° C.) solution of the hydroxy ester of Example 11 (1.12 g 5.0 mmol) and vanadyl acetylacetonate (26 mg, 0.10 mmol) in methylene chloride (20 mL) was added, via syringe, a solution of t-butylhydroperoxide (1.95 mL, 5.12M, 10.0 mmol) in anhydrous isooctane. The solution immediately turned blood red. This mixture was stirred at 0° C. for several hours and then warmed to 25° C. and stirred overnight (TLC, hexane/ethyl acetate:1/1, indicated no starting material remaining). The reaction mixture was diluted with 40 mL of ether and passed through a pad of silica (10 g) to remove the transition metal catalyst. The silica was washed with ether (25 mL) and the filtrate was concentrated to provide a yellow oil which was dissolved in toluene and concentrated. Toluene treatment was repeated until the azeotropic removal of t-butyl hydroperoxide was complete. The crude oil was purified by chromatography (hexane/ethyl acetate:1/1) to provide 1.07 g (89% yield) of the title compound as a colorless oil: R$_f$=0.22 (hexane/ethyl acetate:1/1); $^1$H PMR (CDCl$_3$) δ 5.40 (m, 2H), 3.78 (dd, J=5, 12 Hz, 1H), 3.68 (s, 3H), 3.61 (bs, 1H), 3.50 (bs, 1H), 2.41 (d, J=9 Hz, 1H), 2.38 (m, 2H), 2.18 (q, J=7 Hz, 2H), 2.07 (d, J=12 Hz, 1H), 1.99 (dd, J=4, 12 Hz, 1), 1.22 (m, 2H); $^{13}$C NMR (CDCl$_3$): 173.5, 130.1, 128.5, 74.2, 60.7, 57.1, 51 5, 48.5, 35.8, 33.9, 28.8, 25.1, 22.8 ppm; IR (CHCl$_3$): 3670, 3540, 1730 cm$^{-1}$; Exact mass calculated for C$_{13}$H$_{18}$O$_3$ (M−H$_2$O): 222.1263; Found 222.1256.

EXAMPLE 13

Preparation of methyl 7-(2β-hydroxy-5-oxo-3-cyclopenten-1S,1α-yl)-4Z-heptenoate (13).

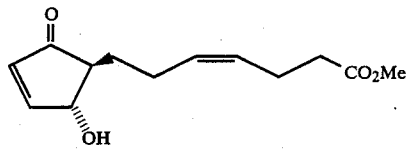

To a cold (−78° C.) solution of distilled oxalyl chloride (1.16 g, 9.18 mmol) in methylene chloride (15 mL, freshly distilled from phosphorous pentoxide under argon) was added, via syringe. dimethyl sulfoxide (920 μL, 1.01 g, 13.00 mmol, distilled from calcium hydride under nitrogen) at such a rate that the internal temperature was maintained below −70° C. After stirring at −78° C. for 15 min, a solution of the compound of Example 12 (2.06 g, 8.58 mmol) in methylene chloride (4 mL) was added dropwise, via syringe, (the internal temperature was maintained below −70° C. throughout the addition). The mixture was stirred at −78° C. for 30 min followed by the dropwise addition, via syringe, of triethylamine (6.01 mL, 4.33 g, 42.90 mmol, freshly distilled). This exothermic reaction was controlled and maintained below −65° C. by adjusting the rate of addition. The reaction was stirred at −78° C. for 3 h and then at 25° C. overnight. The mixture was diluted with ether (150 mL), washed with water (2×20 mL), saturated sodium chloride (25 mL), dried (Na2SO4) snd concentrated to provide 2.0 g (97% yield) of a mixture of the title conpound and methyl 7-(3R-hydroxy-5-oxo-1-cyclopenten-1-yl)-4Z-heptenoate (14) ($R_f$=0.35 and 0.41 respectively, hexane/ethyl acetate:1/1 with 1% acetic acid).

EXAMPLE 14

Preparation of methyl 7-(3R-hydroxy-5-oxo-1-cyclopenten-1-yl)-4Z-heptenoate (14).

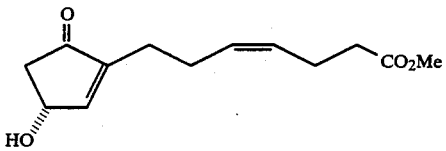

This isomerization of the compound of Example 13 to the desired enone (14) was accomplished according to the method described in an article by G. Stork. *J. Amer. Chem. Soc.* 1975, 97, 3258. To a crude mixture of the compounds formed in Example 13 (5.40 g, 22.7 mmol) and triethylamine (1.15 g, 11.4 mmol, freshly distilled from calcium hydride under nitrogen) in methylene chloride (50 mL) was added a solution of chloral (4.54 mL, 2.27 mmol, 0 5 M in toluene). The resulting homogeneous mixture was stirred at 25° C. for 48 h and then concentrated and azeotropically dried using toluene (2×100 mL) to provide 5.68 g of oil which was purified by medium pressure chromatography (linear gradient elution from ethyl acetate/hexane:1/1 to ethyl acetate/hexane:3/1) to provide 4.70 g (65% based on the compound of Example 12) of the pure title compuund as a colorless oil: $R_f$=0.16 (ethyl acetate/hexane:3/1); $^1$H PMR (CDCl3): δ 7.21 (d, J=3 Hz, 1H). 5.37 (m, 2H), 4.92 (m, 1H), 3.68 (s, 3H), 2.80 dd, J−6, 17 Hz), 2.35 (m, 4H), 2.25 (m, 5H); $^{13}$C (CDCl3): 206.8, 173.9, 157.2, 146.7, 129.9, 128.6, 68.3, 51.7, 44.8, 33.9, 25.1, 24.3, 22.7 ppm;

EXAMPLE 15

Preparation of methyl 7-(5-oxo-3R-[(triethylsilyl)-oxy]-1-cyclopenten-1-yl)-4Z-heptenoate (15).

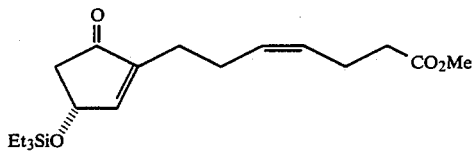

To a solution of the compound of Example 14 (4.68 g, 19.7 mmol), distilled triethylamine (3.10 mL, 2.22 g, 22.0 mmol), and imidazole (1.5 g, 22.0 mmol) in anhydrous dimethylformamide (15 mL, dried over molecular sieves-4A) was added, via syringe, triethylsilyl chloride (3.30 g, 3.67 mL, 22.0 mmol). Initially an ice bath was used to maintain this slightly exothermic reaction at 25° C. and then the reaction was stirred at 25° C. overnight. The reaction mixture was diluted with water (100 mL) and extracted with hexane (1×100 mL, 2×25 mL). The extracts were combined, washed with water (20 mL), saturated sodium chloride (20 mL), dried (Na2SO4), and concentrated to give 7.0 g of an amber oil which was purified by medium pressure chromatography (linear gradient from hexane/ethyl acetate:9/1 to hexane/ethyl acetate:3/1) to provide 6.16 g (89% yield) of the title compound as a colorless oil: $R_f$=0.66 (hexane/ethyl acetate:3/1); $^1$H PMR (CDCl3): δ 7.06 (bd, 1H), 5.39 (m, 2H), 4.89 (m, 1H), 3.67 (s, 3H), 2.76 (dd, J=6, 17 Hz, 1H), 2.35 (m, 4H), 2.32 (dd, 1H), 2.25 (m, 4H); $^{13}$C NMR (CDCl3) 206.0, 173.0, 157.0, 146.4, 129.9, 128.6, 68.7, 34.0, 25.0, 24.5, 22.8, 6.7, 4.7 ppm;

EXAMPLE 16

Preparation of trimethyl {[1-methyl-1S-[3-(tributyl-stannyl)-2E-propenyl]pentyl]oxy}silane, (16).

To a solution of imidazole (20.6 g, 0.30 mole) in dimethylformamide (91 mL) was added chlorotrimethylsilane (24.52 g, 0.23 mole) followed by a solution of 1-(E)-tributylstannyl-4(S)-hydroxy-4-methyloctene (65 g, 0.15 mnole) in dimethylformamide (23 mL). The initial homogeneous reaction mixture was stirred at 25° C. for 1.5 h (during this time the reaction mixture became biphasic). The bilayer solution was transferred to a funnel and the bottom layer (mainly the title compound) was separated and diluted with a cold mixture of hexane (64 mL) and 10% triethylamine in water (32 mL). The upper layer (mainly dimethylformamide) was partitioned with a cold mixture of hexane (64 mL) and 10% triethylamins in water (32 mL). The upper hexane layer was separated and combined with the hexane/triethylamine/water (32 mL) mixture of the title compound. This mixture was partitioned and the hexane layer was washed with 10% triethylamine in water (64 mL), saturated sodium chloride (20 mL), dried (Na2SO4), concentrated and distilled under vacuum using a wiped film evaporator (bp 105° C. at 10−3 mm Hg) providing 31.25 g of the title compound as a colorless oil: $R_f$=0.75 (hexane/ethyl acetate:9/1); $^1$H PMR(CDCl3): δ 6.1–5.8 (m, 2H), 2.30 (d, J=6 Hz, 2H), 1.6–1.2 (m, 18 H), 1.18 (s, 3H), 1.0–0.8 (m, 18H), 0.10 (s, 9H); $^{13}$C NMR (CDCl3) 145.1, 129.4, 75.0, 50.2, 41.2, 28.2, 26.6, 26.4, 25.2, 22.3, 13.20, 12.8, 8.5, 1.70 ppm;

EXAMPLE 17

Preparation of methyl 11R, 16S-dihyrroxy-16-methyl-9-oxoprosta-4Z, 13E-dien-1-oate.

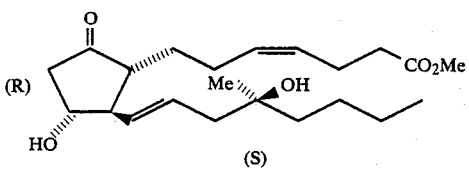

To a cooled (0° C.) suspension of copper cyanide (1.21 g, 13.5 mmol, flame dried under vacuum and cooled under argon) in anhydrous tetrahydrofuran (20 mL) was added, via syringe, methyl lithium (20.6 mL, 29.7 mmol, 1.44 M in diethyl ether, the internal temperature increased to 17° C. and the solution became homogeneous) followed by a solution of the chiral vinylstannane of Example 16 (7.65 g, 15.2 mmol) in dry tetrahydrofuran (20 mL). The resulting violet reaction mixture was stirred at 25° C. for 30 min. An aliquot was withdrawn (0.01 mL) via syringe and added to 0.5 mL of a 1:1 mixture of hexane/(saturated ammonium chloride/concentrated ammonium hydroxide:9/1). After vigorously shaking for 5 min the hexane layer was withdrawn, dried over $K_2CO_3$, and analyzed by gas chromatography for the disappearance of the vinlystannane ($R_t=9.78$) and the formation of methyltributylstannane ($R_t=1.38$ min) and the corresponding octene ($R_t=1.76$ min). After vinylstannane consumption was complete the reaction mixture was cooled to −60° C. and a solution of the chiral enone of Example 15 (3.2 g, 9.0 mmol) in tetrahydrofuran (20 mL) was added ralidly via cannula. After stirring for 3 min the reaction was quenched by pouring the reaction mixture into a vigorously stirred mixture of saturated ammonium chloride/concentrated ammonium hydroxide:9/1 (150 mL) and ethyl acetate (150 mL). The mixture was stirred for 1 h in the presence of air during which time the initial dark brown mixture turned dark blue due to the presence of Cu (II) salts. The layers were separated and the organic layer was washed with saturated sodium chloride (50 mL), dried ($Na_2SO_4$), filtered and concentrated to a mobile yellow oil. The oil was stirred with a mixture of acetic acid/tetrahydrofuran/water:3/1/1 for 1.5 h at 25° C. and then partitioned between ethyl acetate (100 mL) and water (150 mL). The layers were separated and the organic layer was washed with water (2×50 mL) saturated sodium bicarbonate (3×50 mL) and water (50 mL). The combined aqueous washes were back extracted with ethyl acetate (50 mL). The organic layers were combined, washed with saturated sodium chloride (50 mL), dried ($Na_2SO_4$), filtered and concentrated to an oil (9.5 g). The oil was dissolved in a mixture of toluene/heptane:1/1 (100 mL) and added to a vigorously stirred slurry of anhydrous lithium bromide (30 g) in a mixture of toluene/heptane:1/1 (100 mL) under a nitrogen atmosphere. After stirring for 1 h the solvent was removed, via suction, through a porous metal filter. After most of the solvent was removed the lithium bromide complex was resuspended in a mixture of toluene/heptane:1/1 (75 mL) and stirred for 5 min. Stirring was stopped and the solvent was removed as described above. This washing/filtration process was repeated for a total of four times. After the final solvent removal. toluene (100 mL) was added to the lithium bromide complex. To this cooled (10° C.) vigorously stirred slurry was added water (150 mL) at such a rate that the temperature did not exceed 25° C. Stirring was continued for 5 min, the layers were separated and the aqueous layer was extracted with ethyl acetate (150 mL). The organic layers wers combined, washed with saturated sodium chloride (100 mL), dried ($Na_2SO_4$), filtered and concentrated to provide 3.56 g of a viscous oil. Purification using medium pressure chromatography (eluent: ethyl acetate/hexane:40/60 to 100% ethyl acetate using a step gradient) provided 3.51 g (92%) of the title compound, as a colorless oil: $R_f=0.48$ (ethyl acetate); $^1$H PMR (CDCl$_3$) δ 5.73 (dt, J=7, 16 Hz, 1H), 5.41 (dd, J=7, 16 Hz, 1H), 5.35 (m, 2H), 4.05 (apparent q, J=8 Hz, 1H), 3.67 (s, 3H), 3.45 (bs, 1H), 2.72 (dd, J=8, 19 Hz, 1H), 2.40 (dt, J=8, 12 Hz, 1H), 2.35 (m, 4H), 2.24 (dd, J=9, 19 Hz, 2H), 2.15 (m, 2H), 2.0 (dt, J=8, 12 Hz, 1H), 1.62 (m, 2H), 1.48 (bm, 2H), 1.31 (bm, 4H), 1.19 (s, 3H); $^{13}$C (d$_6$-acetone): 215.0, 173.8, 133.5, 129.8, 128.3, 72.5, 71.9, 55.0, 53.9, 51.6, 46.1, 44.9, 41.2, 34.0, 27.6, 27.1, 26.2, 24.5, 23.3, 22.8, 14.1 ppm; IR (CHCl$_{13}$): 3600, 3010, 2920, 2860, 1740, 1600, 1520, 1480 cm$^{-1}$; [α]$_D$= −79.6 (0.817% in CHCl$_3$); Exact mass calculated for $C_{22}H_{34}O_4$(M$^+$-H$_2$O): 362.2680; Found: 362.2610.

EXAMPLE 18

Preparation of methyl 11R,16S-dihydroxy-16-methyl-9-oxoprost-13E-en-1-oate.

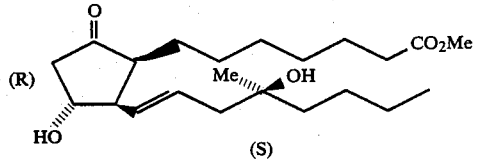

A chiral enone (18) was prepared from the enone of Example 15 by catalytic reduction of the Δ4,5 olefin using Wilkinson's catalyst. The procedure described in Example 17 was used to prepare the title compound, the chiral active isomer of misoprostol, and was produced in 91% yield: $R_f=0.46$ (ethyl acetate); $^1$H PMR (CDCl$_3$) δ 5.7 (dt, 1H), 5.4 (dd, 1H), 4.05 (m, 1H), 3.68 (s, 3H), 3.18 (bs, 1H), 2.7 (dd, 1H), 2.45 (dt, 1H), 2.3 (t, 2H), 2.3-2.15 (m, 2H), 1.95 (m, 1H), 1.2-1.65 (m, 18H), 1.18 (s, 3H), 0.95 (t, 3H); $^{13}$C (CDCl$_3$): 215.8, 174.7, 134.0, 129.7, 73.0, 72.1, 55.1, 54.9, 51.8, 46.5, 45.2, 41.3, 34.3, 29.6, 29.1, 27.8, 27.4, 26.8, 26.6, 25.1, 23.6, 14.4 ppm; IR (CHCl$_3$): 3600, 3010, 2920, 2860, 1740, 1600, 1520, 1480 cm$^{-1}$; [α]$_D$= −61.4 (1% in CHCl$_3$); Exact mass calculated for $C_{22}H_{36}O_4$ (M+ −H2O): 364.2680; Found: 364.2617.

We claim:

1. A compound of the formula

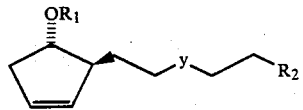

wherein R$_1$ is hydrogen, —COCH$_3$, —COCF$_3$, —COphenyl, or a hydroxyl protecting group selected from tetrahydropyranyl, tetrahydrofuranyl, or tri-lower alkylsilyl;

wherein R$_2$ is

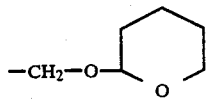

wherein Y is a cis-vinylene, trans-vinylene, or acetylene.

2. A compound according to claim 1 wherein R$_1$ is hydrogen.

3. A compound according to claim 1 of the formula:

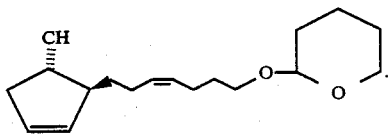

* * * * *

UNITED STATES PATENT AND TRADEMARK OFFICE
CERTIFICATE OF CORRECTION

PATENT NO. : 4,952,710  Page 1 of 2
DATED : August 28, 1990
INVENTOR(S) : Babiak et al.

It is certified that error appears in the above-identified patent and that said Letters Patent is hereby corrected as shown below:

Column 2, lines 15-20, the structure reading  should read 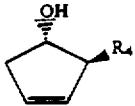

Column 4, the first structure, reading  should read 

Column 5, line 51, reading "thin" should read -- tin --.
Column 10, line 19, reading "allyl" should read -- alkyl --.
Column 10, line 60, reading "-oxethane. methanol" should read
-- -oxethane methanol --.
Column 10, line 67, reading "XXXVII" (2nd occurrence) should read --XXVIII--
Column 11, line 11, reading "slkyl" should read -- alkyl --.
Column 17, line 24, reading "$CrO_3.(C_5H_5N)_2$" should read -- $CrO_3 \cdot (C_5H_5N)_2$ --.
This error regarding the placement of the dot (·) occurs in various situations throughout the remainder of the patent.
Column 18, line 59, reading "of" should read -- for --.
Column 21, line 34, reading "(8 8 g" should read -- (8.8 g --.
Column 21, line 44, reading "1:1" should read -- :1/1--.
Column 21, lines 67-68, reading "uolution of ethylenediamine (2.35 mL."
should read -- solution of ethylenediamine (2.35 L, --
Column 22, the second structure, that portion of the structure reading 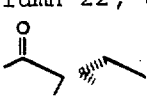 should read 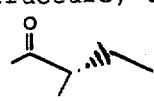

Column 22, line 34, reading "(MgSOhd 4)" should read -- $(MgSO_4)$ --.

Column 22, line 39, reading "J=b 8 Hz" should read -- J=8 Hz --.
Column 22, line 40, reading "1 9-1.3" should read -- 1.9-1.3 --.
Column 23, line 7 , reading "93.7" should read -- 93/7 --.
Column 23, line 9, reading "(m, ?H)" should read -- (m, 2H) --.
Column 23, line 43, reading "hsterogenous mixture was stirred at .25°C."
should read -- heterogenous mixture was stirred at -25° C. --.
Column 24, line 17, reading "b 3-diol" should read -- 3-diol --.

UNITED STATES PATENT AND TRADEMARK OFFICE
CERTIFICATE OF CORRECTION

PATENT NO. : 4,952,710
DATED : August 28, 1990
INVENTOR(S) : Babiak et al.

It is certified that error appears in the above-identified patent and that said Letters Patent is hereby corrected as shown below:

Column 24, line 45, reading "1.9-1 2" should read -- 1.9-1.2 --.
Column 24, line 63, reading "metlylene" should read -- methylene --.
Column 25, line 2, reading "Rf" should read -- $R_f$ --.
Column 25, line 9, reading "1 1" should read -- 1:1 --.
Column 25, line 60, reading "(dt." should read -- (dt, --.
Column 26, line 17, reading "hexsne" should read -- hexane --.
Column 28, line 4, reading "-oxabicyzlo" should read -- -oxabicyclo --.
Column 28, line 38, reading "12 Hz, 1)" should read -- 12 Hz, 1H) --.
Column 28, line 39, reading "51 5" should read -- 51.5 --.
Column 29, line 9, reading "conpound" should read -- compound --.
Column 29, line 44, reading "2.80 dd, J-6" should read -- 2.80 (dd, J=6 --.
Column 30, line 31, reading "mnole" should read -- mmole --.
Column 30, line 58, reading "-dihyrroxy-" should read -- -dihydroxy- --.
Column 31, line 22, reading "ralidly" should read -- rapidly --.
Column 32, the first structure, that portion of the structure reading

 should read 

Signed and Sealed this

Eighteenth Day of August, 1992

Attest:

DOUGLAS B. COMER

Attesting Officer    Acting Commissioner of Patents and Trademarks